(12) United States Patent
Selbig et al.

(10) Patent No.: US 8,935,965 B1
(45) Date of Patent: Jan. 20, 2015

(54) APPARATUS TO ASSIST IN THE COLLECTION OF STORMWATER-QUALITY SAMPLES IN A VERTICAL PROFILE

(75) Inventors: William R. Selbig, Monona, WI (US); Peter E. Hughes, Madison, WI (US); Joel W. Ballweg, Mazomanie, WI (US)

(73) Assignee: The United States of America, as represented by the Secretary of the Department of the Interior, Washington, DC (US)

( * ) Notice: Subject to any disclaimer, the term of this patent is extended or adjusted under 35 U.S.C. 154(b) by 377 days.

(21) Appl. No.: 13/612,108

(22) Filed: Sep. 12, 2012

Related U.S. Application Data

(63) Continuation-in-part of application No. 12/779,549, filed on May 13, 2010, now Pat. No. 8,286,512.

(60) Provisional application No. 61/179,052, filed on May 18, 2009.

(51) Int. Cl.
*G01N 1/12* (2006.01)
*G01N 1/14* (2006.01)
*G01N 1/10* (2006.01)

(52) U.S. Cl.
CPC .......... *G01N 1/14* (2013.01); *G01N 2001/1043* (2013.01)
USPC .................. 73/863.44; 73/863.41; 73/863.51; 73/863.54; 73/863.82; 73/864.81

(58) Field of Classification Search
USPC ............... 73/863.41, 863.43, 863.51, 863.53, 73/863.54, 863.58, 863.82, 864, 864.31, 73/864.81
See application file for complete search history.

(56) References Cited

U.S. PATENT DOCUMENTS

| | | | | |
|---|---|---|---|---|
| 2,388,801 | A | * | 11/1945 | Roetman .................... 73/864.32 |
| 2,926,527 | A | | 3/1960 | Crandall |
| 2,958,222 | A | | 11/1960 | Morgan |
| 2,972,254 | A | | 2/1961 | Lambert |
| 3,224,512 | A | * | 12/1965 | Alexander ...................... 173/19 |
| 3,563,096 | A | * | 2/1971 | Kinkelaar .................. 73/864.32 |
| 3,789,671 | A | | 2/1974 | Larson |

(Continued)

OTHER PUBLICATIONS

Bent, G.C., Gray, J.R., Smith, K.P., and Glysson, G.D., 2000, A synopsis of technical issues for monitoring sediment in highway and urban runoff: U.S. Geological Survey Open-File Report 00-497, 51 p. <http://pubs.usgs.gov/of/2000/ofr00-497/pdf/ofr00497.pdf>.

(Continued)

*Primary Examiner* — David A Rogers
(74) *Attorney, Agent, or Firm* — C. Joan Gilsdorf

(57) ABSTRACT

A sampling method, fluid collection system, and auxiliary sampling device to assist an autosampler in collecting samples from a fluid source. The sampling device includes a support frame and a motorized actuator, with a piston, attached to an end of the support frame. A sample arm has an upper end disposed at an end of the support frame opposite the motorized actuator and a lower end with an inlet to receive a fluid sample. A cable and pulley mechanism links the sample arm to the piston. A fluid conduit within the sample arm has a fluid intake end connected to the inlet and a fluid discharge end connected to an autosampler. The cable and pulley mechanism pivots the sample arm when the motorized actuator pushes or retracts the piston to position the inlet at desired positions within the fluid source so that the autosampler collects multiple samples at various depths.

20 Claims, 10 Drawing Sheets

(56) References Cited

U.S. PATENT DOCUMENTS

| | | |
|---|---|---|
| 3,830,480 A | 8/1974 | Grant |
| 3,929,017 A | 12/1975 | Kowalski |
| 3,940,993 A | 3/1976 | Lapidot |
| 3,962,922 A | 6/1976 | Takeuchi |
| 4,022,059 A | 5/1977 | Schontzler et al. |
| 4,037,476 A | 7/1977 | McCrabb |
| 4,088,025 A | 5/1978 | Foster et al. |
| 4,295,801 A | 10/1981 | Bennett |
| 4,631,968 A * | 12/1986 | Aske ............... 73/864.32 |
| 4,660,422 A | 4/1987 | Eads et al. |
| 4,762,009 A | 8/1988 | Scrudto |
| 4,958,528 A | 9/1990 | Garrison |
| 5,186,052 A | 2/1993 | Gray |
| 5,211,062 A | 5/1993 | Moser |
| 5,279,151 A | 1/1994 | Coody et al. |
| 5,299,141 A | 3/1994 | Hungerford et al. |
| 5,347,877 A | 9/1994 | Gadbois |
| 5,435,399 A | 7/1995 | Peterson et al. |
| 5,463,909 A | 11/1995 | Eldridge |
| 5,587,539 A | 12/1996 | Carpenter |
| 5,606,138 A | 2/1997 | Saarenketo |
| 5,652,397 A | 7/1997 | Dawson et al. |
| 5,693,894 A | 12/1997 | Jobson |
| RE35,824 E | 6/1998 | Welker |
| 5,783,758 A | 7/1998 | Dudley |
| 5,811,696 A | 9/1998 | Jobson |
| 5,844,148 A | 12/1998 | Klein et al. |
| 6,237,429 B1 * | 5/2001 | Melnyk ............ 73/864.45 |
| 6,357,305 B1 * | 3/2002 | Witt et al. ......... 73/863.53 |
| 6,742,404 B2 | 6/2004 | Smith et al. |
| 7,377,189 B2 | 5/2008 | Champseix et al. |
| 2010/0037712 A1 * | 2/2010 | Burton ............. 73/863.11 |

OTHER PUBLICATIONS

Smith, K.P., 2002, Effectiveness of three best management practices for highway-runoff quality along the southeast expressway, Boston, Massachusetts: U.S. Geological Survey Water-Resources Investigations Report 02-4059, 62 p. <http://pubs.usgs.gov/wri/wri024059/pdfs/wri024059.pdf>.

Kayhanian, M., Young, T., and Stenstrom, M., 2005, Limitation of current solids measurements in stormwater runoff, Stormwater, v. 6, No. 5, p. 40-58. <http://www.stormh2o.com/july-august-2005/solids-measurements-runoff.aspx>.

DeGroot, G.P., Gulliver, J.S., and Mohseni, O., 2009, Accurate sampling of suspended solids, ASCE Conf. Proc. 342, 81 (2009).

* cited by examiner

APPARATUS TO ASSIST IN THE COLLECTION OF STORMWATER-QUALITY SAMPLES IN A VERTICAL PROFILE

CROSS-REFERENCE TO RELATED APPLICATION(S)

This application is a continuation-in-part of U.S. patent application Ser. No. 12/779,549, filed on May 13, 2010, which claims the benefit of U.S. Provisional Patent Application Ser. No. 61/179,052, filed on May 18, 2009, both of which are hereby incorporated by reference in their entirety.

STATEMENT OF GOVERNMENT INTEREST

The invention described herein may be manufactured, used, and licensed by or for the U.S. Government for governmental purposes without payment of any royalties thereon.

BACKGROUND

The publications and other materials referred to herein by author and date are incorporated herein by reference, and are listed alphabetically by author in the appended bibliography.

This application relates in general to fluid samplers and, in particular, to the automated collection of stormwater-quality samples in a vertical profile.

Sediment is a pollutant in rivers, streams, lakes, and reservoirs that can destroy aquatic habitats and affect our drinking water and recreational activities such as swimming. Many of today's environmental policies are oriented towards controlling the quantity of sediment and sediment-associated constituents from not only large rural watersheds but also smaller urban drainage basins into receiving waters. These policies are based upon scientific research designed to characterize and quantify the presence of a suite of regulated contaminants. Proper characterization depends on the collection, processing, and analysis of accurate concentration data.

Autosamplers are widely used to collect stormwater-quality samples where the remoteness or inaccessibility of a study site precludes manual collection. Additionally, autosamplers can be programmed to acquire samples in an environment that is rapidly changing, such as is the case when sampling urban runoff. The collection of a representative stormwater-quality sample in urban runoff can be difficult due to large sources of variability, both temporal and spatial (Selbig and Bannerman, 2007; Horowitz, 1995). Use of automated stormwater-quality samplers has vastly improved the way water resources professionals collect samples in these environments. However, these automated pumping systems do not always collect a representative aliquot of the flow moving past the sample intake, resulting in biased concentration data (Smith, 2002; Fowler et al., 2009).

SUMMARY

One of the sources of such non-representative samples is the settling of sediments in flows. A study conducted by the inventors collected and characterized data derived from stormwater-quality samples from urban basins. The intakes of autosamplers were located at different vertical locations in the water column, including approximately 1 inch off the pipe invert and at 30 and 60 percent of the water level. The inventors observed from the resulting sediment concentration and particle size distribution data that larger particles tend to concentrate near the bottom of the pipe. In general, concentrations of suspended sediment decreased with increasing vertical distance from the storm sewer invert. Similarly, median particle sizes also decreased with increasing distance from the pipe floor. As energy of flow increases with increasing discharge, stratification of sediment size and concentration become more apparent, suggesting vertical stratification of solids by particle size in the flowing water column of storm sewer runoff.

Typically, the intake orifice of an autosampler is located near the pipe floor to capture low flow conditions. The recommended intake orifice diameter for automated samplers is approximately $3/8$-inch (Teledyne ISCO, 2008). Therefore, in large diameter pipes, the stormwater-quality sample collected by the autosampler represents only the bottom $3/8$-inch of the pipe. During higher flows, the majority of the water column is not sampled. Even in circular pipes with a diameter as small as 1 foot, the concentration and distribution of sediment is concentrated near the bottom of the pipe over a range of flow conditions (Smith, 2002). Thus, resulting concentration data and particle size distributions using the suggested autosampler installation configurations could bias towards larger particles that tend to accumulate near the bottom of a pipe or other conveyance.

The ability of an autosampler to collect a representative stormwater-quality sample has relied upon proper mixing of the flow stream prior to sampling. This would disperse all sediment into a homogenous mixture rendering the location of sample acquisition in the water column irrelevant. However, the energy required to distribute coarse material homogenously throughout the water column is insufficient under normal flow conditions (Clark et al., 2008). Coarse particles with high specific density become stratified and tend to be transported along the bottom of the pipe floor. Attempts to artificially provide agitation in the flow path to produce a sample representing the average concentration of suspended sediment have proved unsatisfactory (Smith, 2002). Since introduction of objects in the flow path can often alter the hydrology by slowing down flow, and thus allowing sediment to settle out of suspension, most efforts for a homogenous runoff mixture are focused at a nearby outfall. However, site conditions or study requirements may preclude sampling at an outfall. Also, in an urban environment, the energy required to transport sediment in a pipe via increased flow can change rapidly such that sediment moving as bedload can quickly be carried as suspended load, and vice versa. Therefore, proper characterization of the distribution of particles in urban runoff requires the collection of water-quality samples from multiple, rather than a single fixed point in the water column.

In accordance with the invention, then, there is provided a liquid sampling method, assembly, and device to assist an autosampler in collecting stormwater-quality samples that are more representative of the entire water column. Stormwater-quality sampling in a pipe is traditionally done by installing a single sample tube at a fixed point near the bottom of a pipe. Described herein is an auxiliary sampling device for use with an autosampler that improves upon this concept by connecting the sample tube to the described device so that stormwater-quality samples can be acquired from a single or multiple points in the water column. Integrating data from multiple points spaced vertically throughout the water column, rather than using a single, fixed point, results in a more accurate representation of stormwater-borne solids.

In accordance with one embodiment of the invention, a fluid sampling device has a support frame and a motorized actuator, with a piston, attached to an end of the support frame. A sample arm has an upper end disposed at an end of the support frame opposite the motorized actuator and a lower end with an inlet to receive a fluid sample from a fluid source.

A cable and pulley mechanism links the sample arm to the piston. A fluid conduit within the sample arm has a fluid intake end connected to the inlet and a fluid discharge end connected to an autosampler. The cable and pulley mechanism vertically pivots the sample arm when the motorized actuator pushes or retracts the piston to position the inlet at desired positions within the fluid source so that the autosampler collects multiple samples at various depths.

In accordance with another embodiment, a method of collecting samples from a fluid source using an autosampler includes assembling an auxiliary sampling device by providing a support frame having a front end and a rear end; attaching a motorized actuator with a piston to the rear end of the support frame; providing a rotatable sample arm having an upper end disposed at the front end of the support frame and a lower end with an inlet to receive a fluid sample from a fluid source; connecting a cable and pulley mechanism between the sample arm and the piston; and placing a fluid conduit, having a fluid intake end and a fluid discharge end, within the sample arm, and connecting the fluid intake end to the inlet to receive the fluid sample and connecting the fluid discharge end to an autosampler. The motorized actuator is controlled to push or retract the piston, while the movement of the piston is translated into pivotal movement of the sample arm to position the inlet at a desired level within the fluid source. Fluid is drawn up the fluid conduit to the autosampler. The motorized actuator is repeatedly controlled to position the inlet of the sample arm at various levels within the fluid source to collect multiple samples.

In accordance with another embodiment, a fluid collection system includes an autosampler and an auxiliary sampling device. The auxiliary sampling device includes a support frame, a motorized actuator, a sample arm, and a cable and pulley mechanism. The motorized actuator has a piston and is attached to an end of the support frame. The sample arm has an upper end disposed at an end of the support frame opposite the motorized actuator and a lower end with an inlet to receive a fluid sample from a fluid source. The cable and pulley mechanism connects the sample arm to the piston. A fluid conduit within the sample arm has a fluid intake end connected to the inlet and a fluid discharge end connected to the autosampler. The cable and pulley mechanism vertically pivots the sample arm when the motorized actuator pushes or retracts the piston to position the inlet at desired positions within the fluid source so that the autosampler collects multiple samples at various depths.

Thus, the auxiliary sampling device described herein relates to the automated collection of stormwater-quality samples at one or more depths in a vertical profile. The collection of stormwater-quality samples at multiple depths provides a composite sample that is more representative of the entire water column.

BRIEF DESCRIPTION OF THE DRAWINGS

Various aspects and advantages of the invention will become apparent from the following detailed description, taken in conjunction with the accompanying drawings. The drawings are not necessarily drawn to scale. In the drawings.

DETAILED DESCRIPTION OF THE PREFERRED EMBODIMENTS

The general field of application of the liquid sampling method, assembly, and auxiliary sampling device described herein is intended to be in closed structures used to convey stormwater runoff in an urban environment, such as storm sewers, and embodiments of the invention will be described in this context. However, the invention may also be used in any water-quality sampling environment where the distribution of sediment in flow can be shown to be heterogeneous and not easily corrected using established manual sampling techniques (e.g., equal width increment sampling and equal depth increment sampling).

Figure 1:
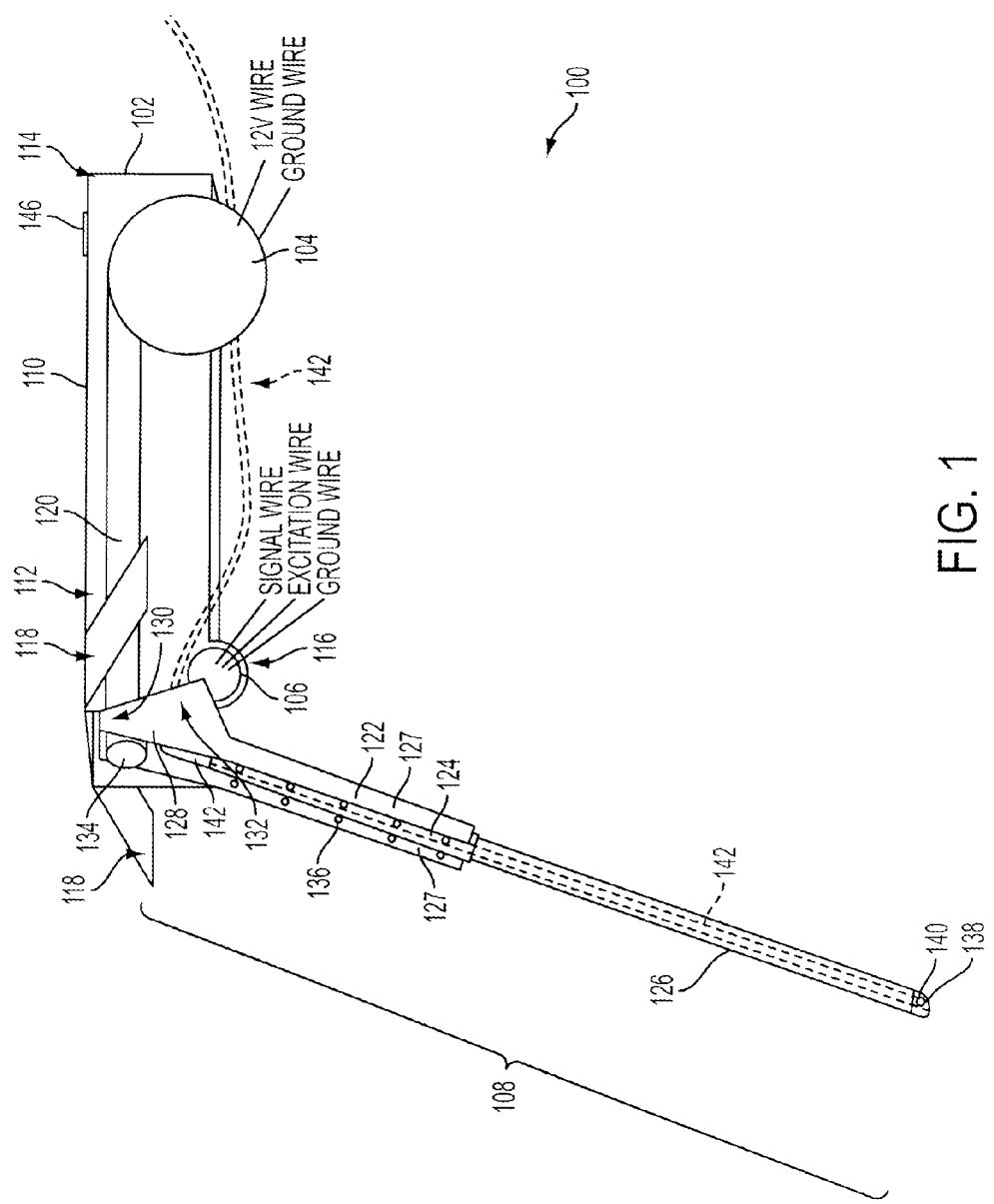
FIG. 1 shows a side view of an auxiliary sampling device embodying the principles of the invention in accordance with one embodiment of the invention.
Figure 2:
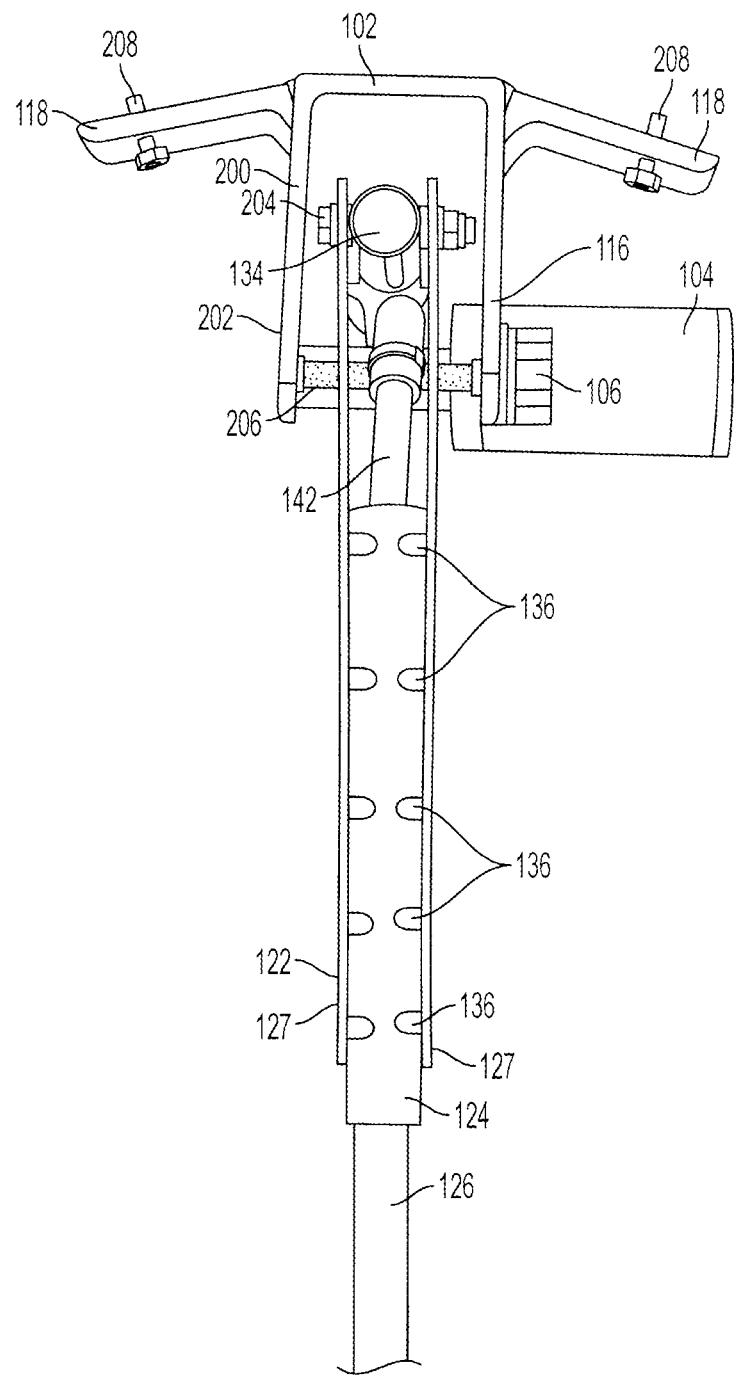
FIG. 2 shows a front view of the auxiliary sampling device of FIG. 1.
Figure 3:
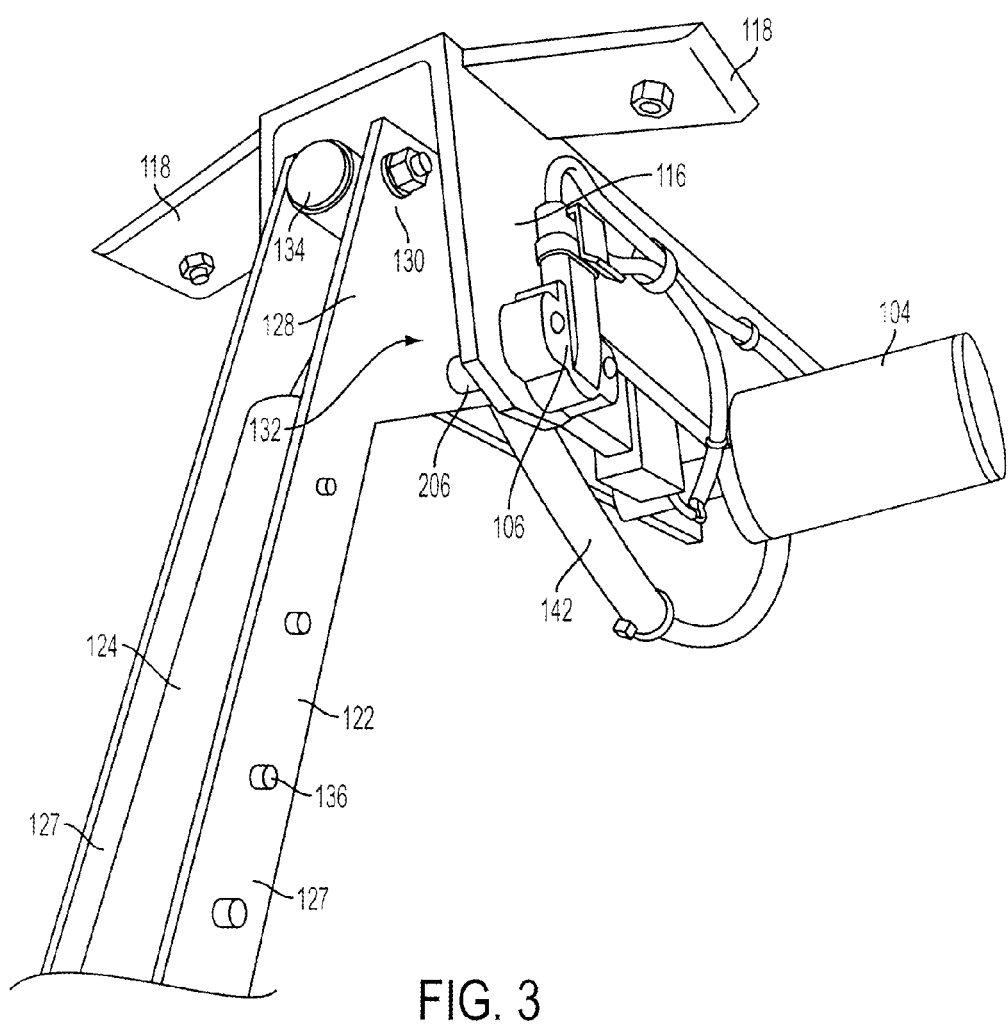
FIG. 3 shows a perspective view of the right side of the auxiliary sampling device of FIG. 1.
Figure 4:
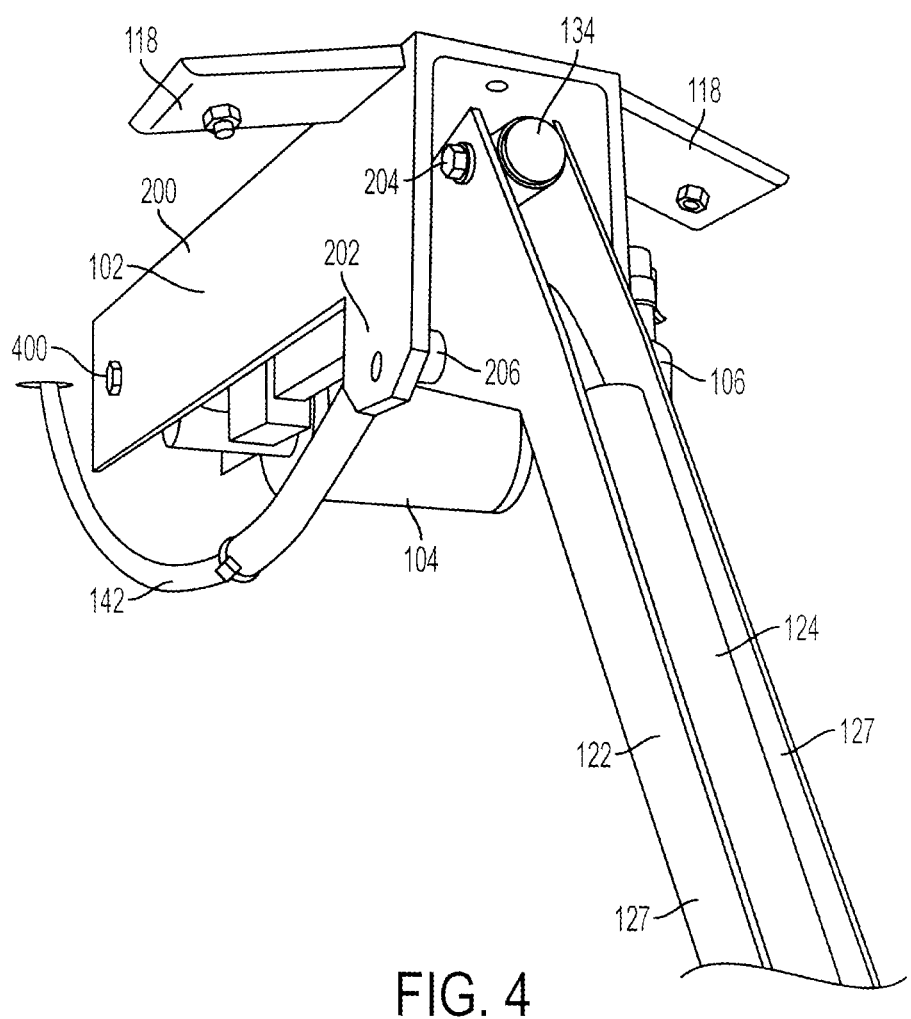
FIG. 4 shows a perspective view of the left side of the auxiliary sampling device of FIG. 1.

Referring to FIGS. 1 through 4, there is shown an exemplary auxiliary sampling device 100 of the present invention. FIG. 1 shows a side view of the auxiliary sampling device 100 in accordance with one embodiment of the invention. FIG. 2 shows a front view of the auxiliary sampling device 100. FIGS. 3 and 4 show right and left sides, respectively, of the auxiliary sampling device 100. The auxiliary sampling device 100 has a support frame 102, a motorized piston 104 (also referred to as a linear actuator or a ball drive actuator), a rotary potentiometer 106, and a sample arm assembly 108. The support frame 102, made of a material such as aluminum or stainless steel, has a top mounting plate 110 that is mounted to the ceiling or headwall of a storm sewer (such as storm sewer 800 illustrated in FIG. 8). The mounting plate 110 has a front portion 112 and a back portion 114. A side plate 200 (FIGS. 2 and 4) extends downward from the left side of the mounting plate 110. A first leg 202 extends downward from the side plate 200 at the front portion 112 of the mounting plate 110. A second leg 116 extends downward from the front portion 112 of the mounting plate 110 opposite the first leg 202 (FIGS. 1 and 3). Mounting brackets 118 project outward from the sides of the front portion 112 of the mounting plate 110.

The motorized piston 104, such as the 12 VDC motorized piston manufactured by Motion Systems Corporation, Eatontown, N.J., has a mounting eyelet (such as mounting eyelet 514 illustrated in FIGS. 5 and 6) for attachment to the support frame 102, and a piston 120 that it pushes or retracts, depending on DC voltage polarity. The piston 120 preferably has an extension length of about four inches. The motorized piston 104 is secured to the support frame 102 using a motorized piston mount 400 (FIG. 4) such as a threaded bolt that is inserted through the mounting eyelet 514 and secured to the side plate 200.

The sample arm assembly 108 includes a stabilizing channel 122, a housing 124, and a shaft 126. As shown in the embodiment of FIGS. 1 to 3, the stabilizing channel 122 is constructed of two elongated, flat metal plates, such as aluminum or stainless steel plates, that form the sides 127 of the stabilizing channel 122. Each side 127 of the stabilizing channel 122 has an upper member 128 with an upper end 130 and a flange 132 extending from the upper member 128. The upper end 130 of each upper member 128 is attached to a terminus 134 of the piston 120 by threading a piston mount 204 such as a threaded bolt (FIG. 2) through holes in each of the sides 127 of the stabilizing channel 122 and through a hole in the piston 120. Each flange 132 is attached to a potentiometer axle 206 (also referred to as a "pivot member"). The potentiometer axle 206 is supported on each end by the first leg 202 and the second leg 116 of the support frame 102 (FIGS. 2 to 4). One end of the potentiometer axle 206 is connected to the potentiometer 106. As the piston 120 extends or retracts, it pivots the stabilizing channel 122 around the potentiometer axle 206. This allows the potentiometer 106 to measure the rotational position of the stabilizing channel 122 as it pivots up or down. The potentiometer 106 may be scaled or calibrated to meet the parameters for each individual field setting. The full rotational range of the stabilizing channel 122 (and thus the sample arm assembly 108) is 90 degrees traveling from completely vertical to completely horizontal.

The housing 124 is attached to the inside of the stabilizing channel 122. In the embodiment shown in FIGS. 1 through 4, the housing 124 is a 1.5×0.625-inch elliptical, stainless steel housing that is welded to the stabilizing channel 122. The shaft 126 is inserted into the lower end of the housing 124 and secured in place with fasteners such as a series of set screws 136 that push the shaft 126 against the housing 124. In the embodiment shown in FIGS. 1 through 4, the shaft 126 is a 1.25×0.375-inch elliptical, stainless steel shaft. The shaft 126 may be adjusted up or down within the housing 124 by adjusting the set screws 136 so that the bottom end of the shaft 126 reaches the floor of the storm sewer 800.

At the terminus of the shaft 126 is an end cap 138 (FIG. 1), made of an inert material such as polycarbonate, with opposing intake orifices 140. The end cap 138 is secured to the shaft 126 by compression fitting. The intake orifices 140 are formed by drilling two holes on opposing sides of the end cap 138 so that flow moves parallel to each orifice opening. In the embodiment shown in FIG. 1, the intake orifices 140 are both 0.25-inch inner diameter (ID) holes. Water is drawn from the source through the intake orifices 140 into a sample tube 142 located inside the shaft 126. In the embodiment shown in FIG. 1, the sample tube 142 has a 0.375-inch inner diameter and is made of flexible polyethylene. The sample tube 142 is connected to the end cap 138 by insertion into a hole drilled in the top of the end cap 138. For example, a 0.5-inch outer diameter hole may be drilled in the top of the end cap 138 to receive the sample tube 142 having a 0.375-inch ID. The sample tube 142 and its connection to the end cap 138 are contained within the shaft 126. The sample tube 142 extends continuously from the end cap 138 up through the shaft 126 and the housing 124, over the potentiometer axle 206, and underneath the piston 120. The sample tube 142 is then routed to an autosampler (such as autosampler 802 illustrated in FIG. 8). The autosampler may be manufactured by Teledyne ISCO, Lincoln, Nebr., for example.

The support frame 102 is mounted to the ceiling of the storm sewer 800 (FIG. 8) using appropriate fasteners such as concrete anchors 208 (FIG. 2). The concrete anchors 208 hold the support frame 102 to the storm sewer 800 at the back portion 114 of the support frame 102 through a rear mounting hole 146 (FIG. 1) and at the front portion 112 of the support frame 102 through the mounting brackets 118.

Figure 5:
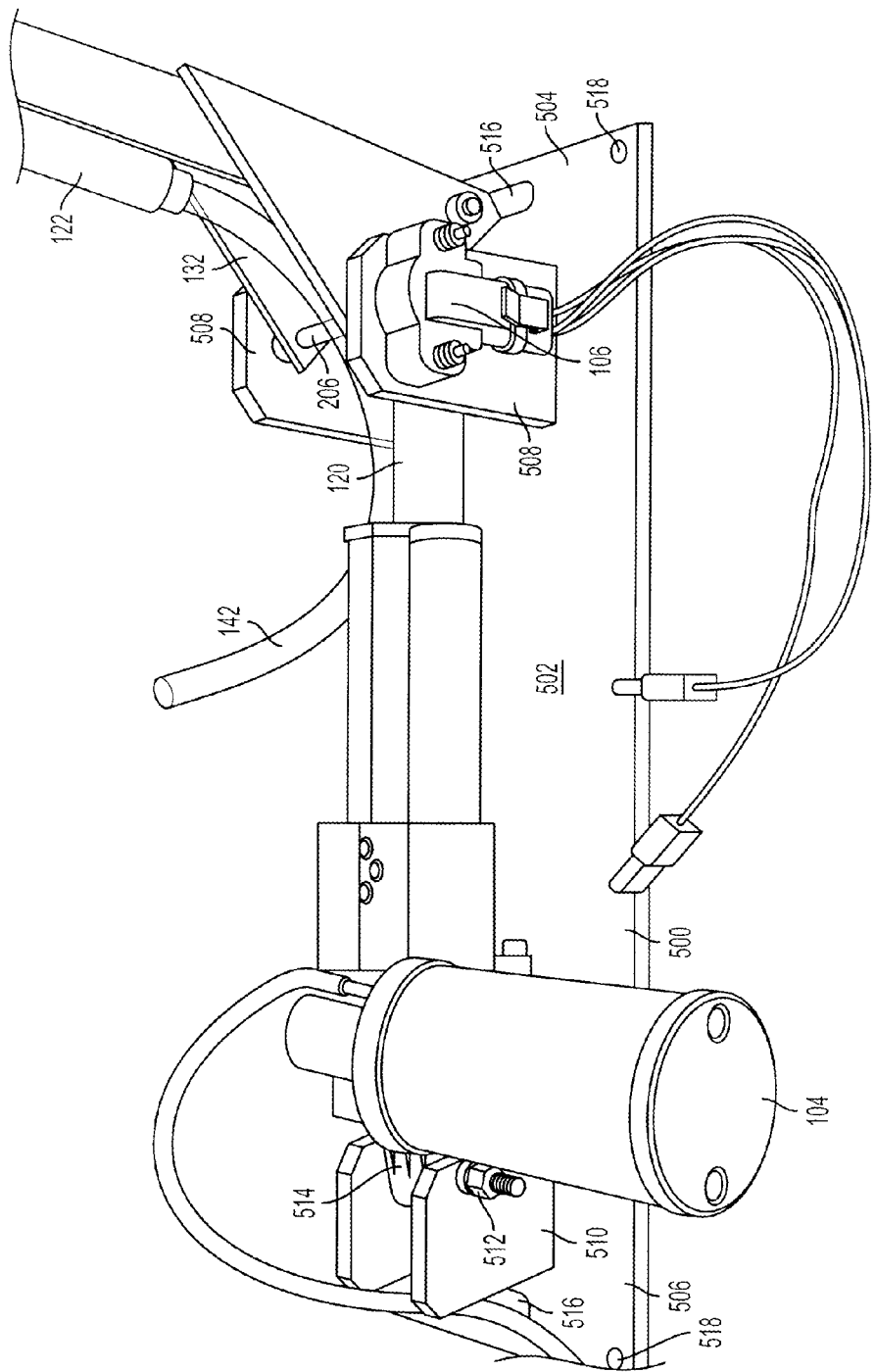
FIG. 5 shows a perspective view of an underside of a support frame in accordance with another embodiment of the invention.
Figure 6:
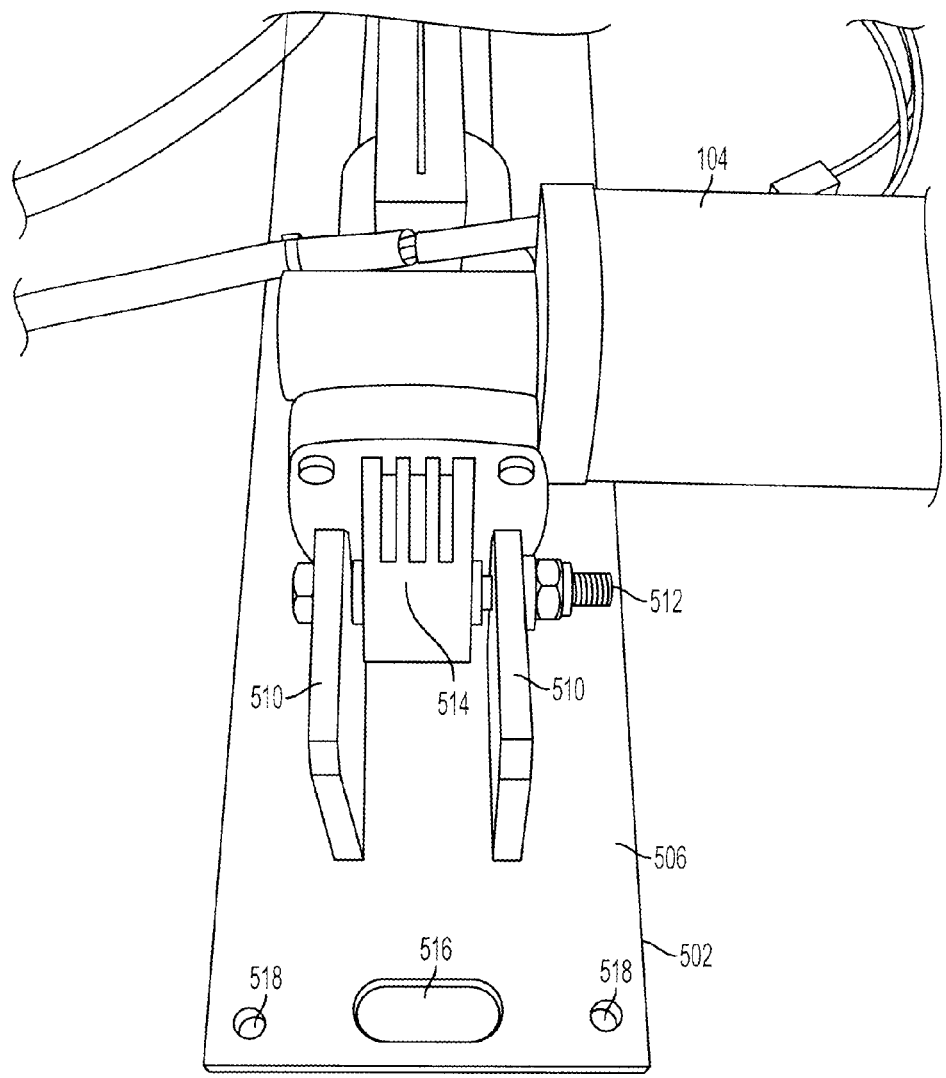
FIG. 6 shows a back portion of the underside of the support frame of FIG. 5.
Figure 7:
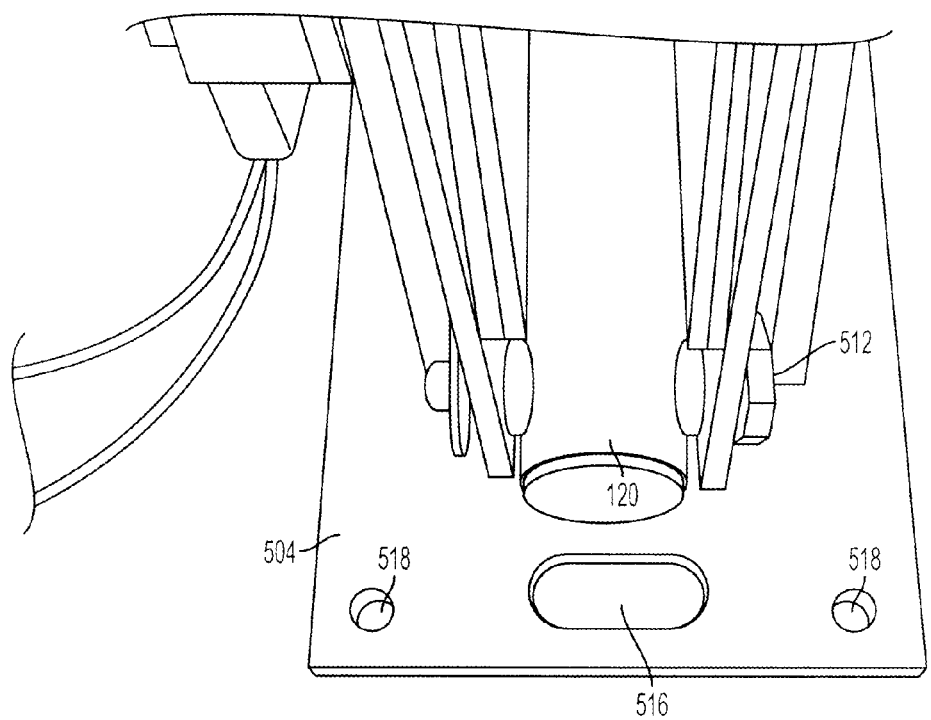
FIG. 7 shows a front portion of the underside of the support frame of FIG. 5.

FIG. 5 shows the underside of another support frame 500 according to an alternative embodiment. In the embodiment shown in FIG. 5, the support frame 500 has a mounting plate 502 with a front portion 504 and a back portion 506. Front legs 508 extend from the front portion 504 and back legs 510 extend from the back portion 506. The potentiometer axle 206 is supported on each end by the front legs 508 of the support frame 500. FIG. 6 shows the back portion 506 of the support frame 500, and FIG. 7 shows the front portion 504 of the support frame 500. As shown in FIG. 6, the motorized piston 104 is secured to the support frame 500 by threading a mounting bolt 512 through the back legs 510 and through the mounting eyelet 514. In this embodiment, the concrete anchors 208 hold the support frame 500 to the storm sewer 800 through center-line anchor slots 516 located at the front portion 504 (FIG. 7) and the back portion 506 (FIG. 6) of the mounting plate 502. The center-line anchor slots 516 allow the mounting plate 502 to be swiveled to the left or right a few centimeters to adjust the sample arm assembly 108 so that it is positioned in the center of the storm sewer 800. Once the support frame 500 is anchored to the ceiling of the storm sewer 800, it can be adjusted to a level position by inserting lateral-stabilizer bolts (not shown) through holes 518 located at each corner of the support frame 500, again to position the sample arm assembly 108 so that it is placed in the center of the storm sewer 800. The lateral-stabilizer bolts also act as stabilizers so that when the support frame 500 is positioned correctly, these bolts are threaded securely up against the ceiling of the storm sewer 800 at all four corners.

Figure 8:
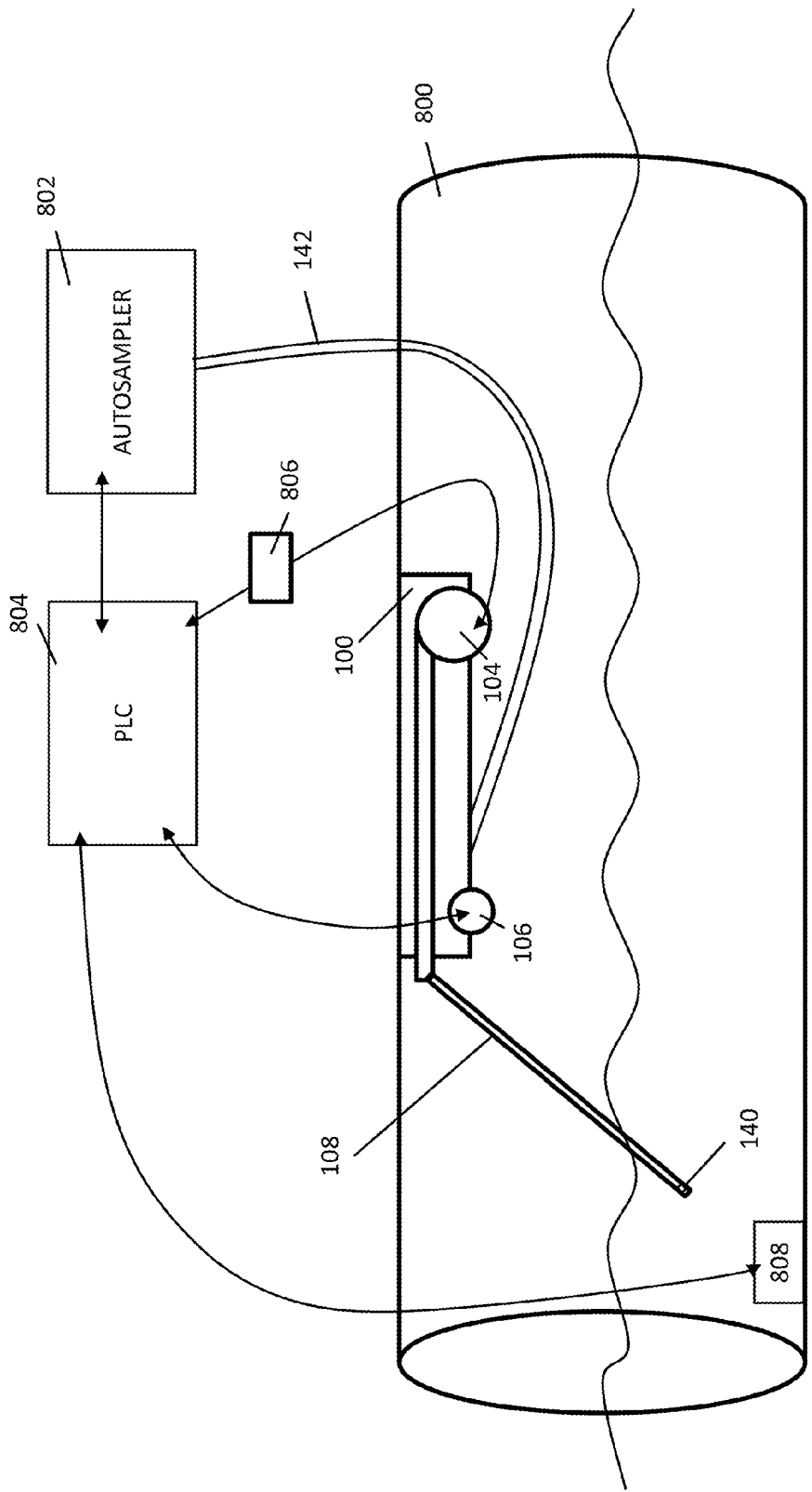
FIG. 8 shows a schematic representation of the auxiliary sampling device of FIG. 1 attached to the ceiling of a storm sewer.

FIG. 8 shows a general view of the auxiliary sampling device 100 within the storm sewer 800. The rotation of the sample assembly arm 108, and thus the position of the intake orifices 140, is controlled by an external datalogger or other programmable logic control (PLC) device 804, that activates a double-pole, double-throw relay 806 to energize the motorized piston 104. The PLC 804, the relay 806, and the autosampler 802 are located above ground in a weatherproof enclosure (not shown).

The PLC 804 may be programmed to set the intake orifices 140 to a percentage of the water depth. The vertical position of the intake orifices 140 is determined using a $5^{th}$-order polynomial scaled to represent water depth as a function of voltage. To calibrate the potentiometer 106 to site conditions, a user directs the potentiometer 106 to move to a target position manually. Once the sample arm assembly 108 has moved to that position, the depth of the intake orifices 140 above the floor of the storm sewer 800 is measured. This process is repeated for multiple target positions until a sufficient number of data points has been determined to develop a polynomial regression. Between five and ten data points are preferably determined.

The depth of water is measured by an acoustic-velocity sensor 808, or similar device. The acoustic velocity sensor 808, such as an acoustic velocity sensor manufactured by Teledyne ISCO, Lincoln, Nebr., is a low-profile sensor that is mounted to the floor of the storm sewer 800. An attached cable is routed up from the acoustic-velocity sensor 808 to the PLC 804. Upon initiation of a stormwater-quality sample, the PLC 804 uses the instantaneous water depth measured by the acoustic-velocity sensor 808 to compute a target voltage using the $5^{th}$-order polynomial. The PLC 804 then activates the motorized piston 104 to move the piston 120 forward or backward until the potentiometer 106 reaches the target voltage. For example, if the target sample position is set to be 50% of an actual water depth of 0.5 feet, then the PLC 804 will activate the motorized piston 104 until the potentiometer 106 reads the voltage representing 0.25 feet.

Thus, the motorized piston 104 rotates the sample arm assembly 108 to any vertical depth within the storm sewer 800. Once the PLC 804 determines that the potentiometer 106 has reached the target voltage, the PLC 804 controls the autosampler 802 to operate with normal purge/withdraw cycles to collect a stormwater-quality sample and deposit it in one or more storage containers. Once the sample has been acquired, the sample arm assembly 108 either moves to a new position for collection of another sample or fully retracts to the horizontal position, which removes the sample arm assembly 108 from the flow path. Any debris that may have accumulated on the sample arm assembly 108 while acquiring a sample is cleared away by water discharging past the sample arm assembly 108 as it retracts into the horizontal position.

Figure 9:
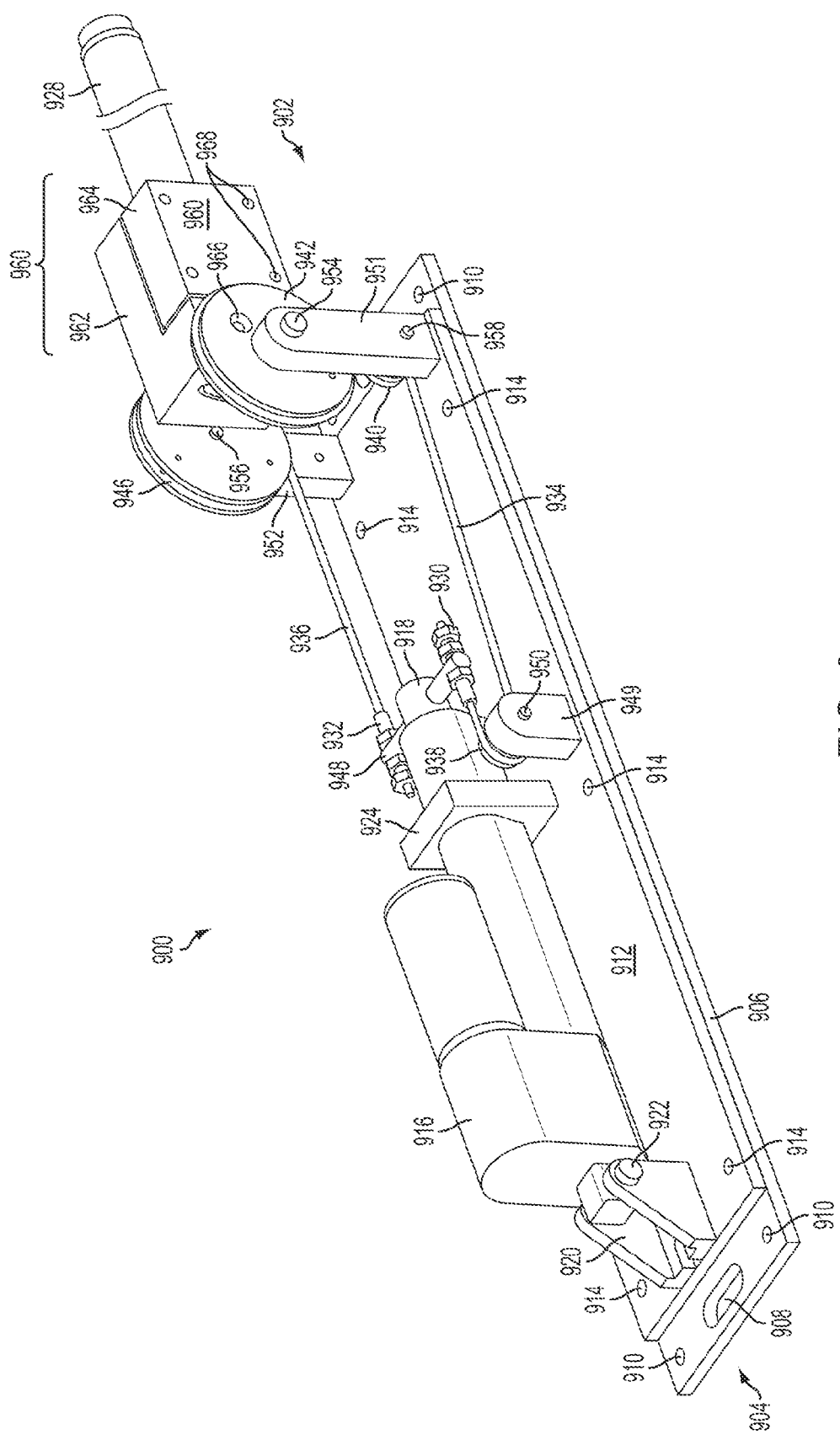
FIG. 9 shows a perspective view of an underside of an auxiliary sampling device in accordance with a third embodiment of the invention.

FIG. 9 shows the underside of an auxiliary sampling device 900 according to another embodiment. The auxiliary sampling device 900 has a front end 902 and a rear end 904. A primary support frame 906 is mounted to the ceiling of the storm sewer 800 by inserting fasteners such as concrete anchors (not shown) through center-line anchor slots 908 located at the front end 902 and the rear end 904. Fasteners such as threaded bolts (not shown), inserted into the ceiling of the storm sewer 800 through holes 910 located at each corner of the primary support frame 906, are adjusted in and out to accommodate various site conditions and provide lateral stability. A secondary support frame 912 is attached to the primary support frame 906 using threaded bolts (not shown) inserted into holes 914 drilled near the edges of the secondary support frame 912 and the primary support frame 906. The primary support frame 906 and the secondary support frame 912 are made of a material such as aluminum.

The back of a motorized actuator 916 (such as the 12 VDC linear motorized actuator, with a piston having an extension length of about four inches, manufactured by Firgelli Automations, Bellingham, Wash.) with a piston 918 and an internal potentiometer is secured to the secondary support frame 912 at the rear end 904 using, for example, a clevis mounting bracket 920 and a threaded bolt or locking pin 922. The front of the motorized actuator 916 is secured to the secondary support frame 912, for example, using a fitted sleeve 924 welded to the secondary support frame 912. The motorized actuator 916 pushes or retracts the piston 918 depending on DC voltage polarity.

A cable and pulley mechanism is used to rotate a sample arm 928. The cable and pulley mechanism includes tensioners 930 and 932, cables 934 and 936, small pulleys 938 and 940, and large pulleys 942 and 946. The small pulleys 938 and 940 have diameters of about 0.625 inches and the large pulleys 942 and 946 have diameters of about 2.546 inches. The cable and pulley mechanism is attached to the terminus of the piston 918 using a pin 948 inserted through a hole at the terminus of the piston 918. The tensioners 930 and 932 are attached to the pin 948 on either side of the terminus of the piston 918 and the cables 934 and 936 are attached respectively to the tensioners 930 and 932. A mounting bracket 949 is attached to the secondary support frame 912 near the terminus of the motorized actuator 916. The small pulley 938 is attached to the mounting bracket 949 using a pin 950. Two mounting brackets 951 and 952 are attached to the secondary support frame 912 at the front end 902. The pulleys 942 and 946 are attached, respectively, to the terminus of each mounting bracket 951 and 952 using pins 954 and 956. The small pulley 940 is attached to the mounting bracket 951 beneath the large pulley 942 using a pin 958. All of the pulleys, brackets, and pins are made of a material such as aluminum. The cables 934 and 936 are made of a material such as stainless steel.

A compression sleeve 960 made of a material such as plastic and having an L-shaped member 962 and an accompanying locking plate 964 is secured between the two large pulleys 942 and 946 using fasteners such as stainless steel screws 966. The L-shaped member 962 and the locking plate 964 fit around an upper end of the sample arm 928 to lock the sample arm 928 securely in place by compression with fasteners such as set screws 968. This allows the sample arm 928 to be easily adjusted up or down to reach the floor of the storm sewer 800 when in a vertical position. As the piston 918 extends or retracts, the cables 934 and 936 move around the small pulleys 938 and 940 and the large pulleys 942 and 946 to rotate the sample arm 928 up or down within a range of about 0 to about 170 degrees. The potentiometer, internalized within the motorized actuator 916, measures the rotational position of the sample arm 928 as it pivots up or down.

Figure 10:
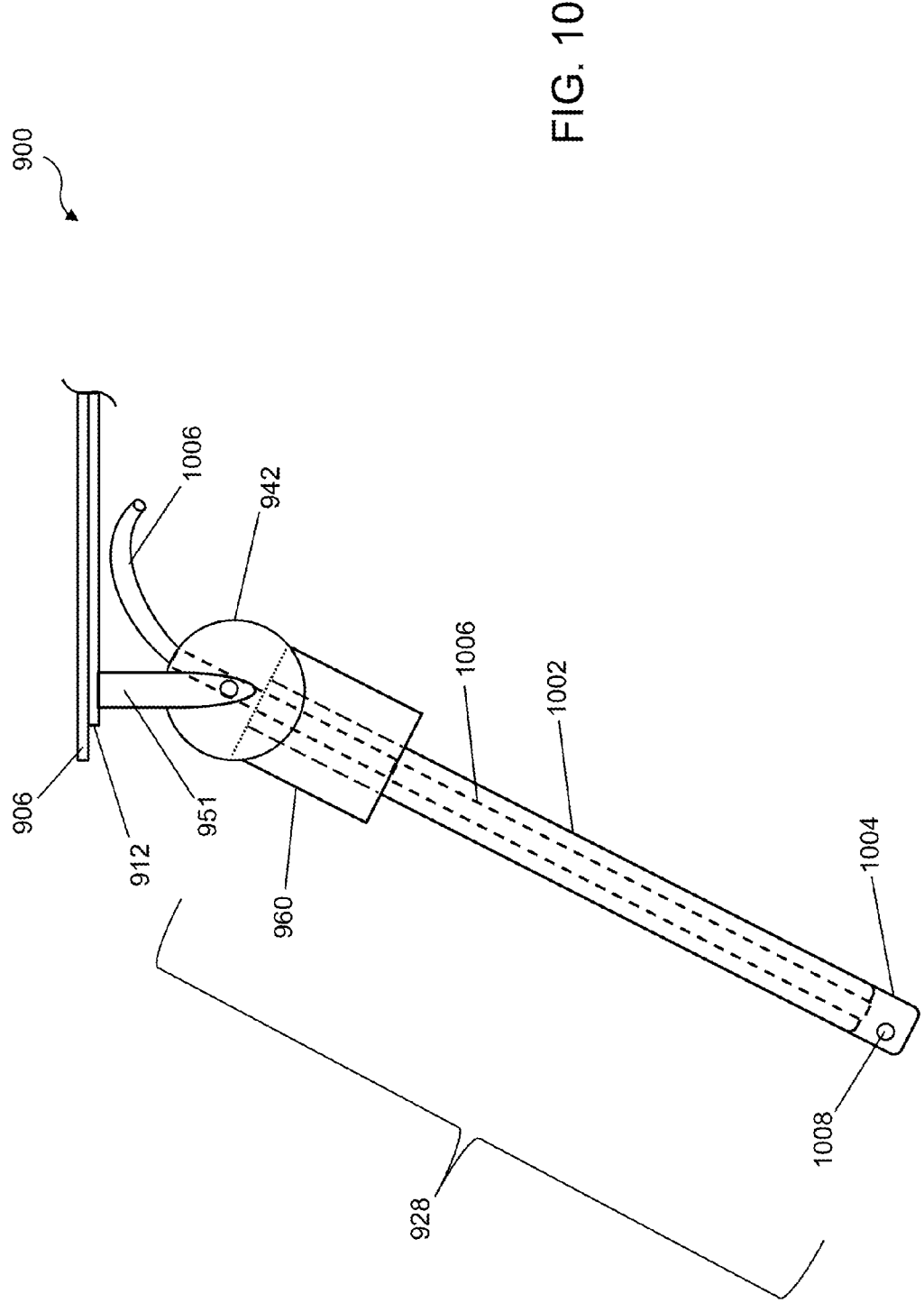
FIG. 10 shows a partial side view of the auxiliary sampling device of FIG. 9.

FIG. 10 shows a partial side view of the auxiliary sampling device 900. As shown in FIG. 10, the sample arm 928 includes a shaft 1002 and an end cap 1004. The shaft 1002 is a section of streamline tubing of desired length (i.e., having a length sufficient to reach the floor of the storm sewer 800 when in a vertical position) with a major axis of about 1.18 inches, a minor axis of about 0.5 inches, and a wall thickness of about 0.035 inches. The upper end of the shaft 1002 is held in place by the compression sleeve 960. The lower end of the shaft 1002 receives the end cap 1004. A sample tube 1006 made of a material such as stainless steel and having an inner diameter (ID) of about 0.25 inches is inserted through the shaft 1002 and extends from the lower end of the shaft 1002 to approximately three inches beyond the compression sleeve 960.

The end cap 1004, made of a material such as polycarbonate, has opposing intake orifices 1008. The end cap 1004 is secured to the sample tube 1006 as well as the shaft 1002 by friction fit. The intake orifices 1008 are formed by drilling two holes on opposing sides of the end cap 1004 so that flow moves parallel to each orifice opening 1008. In the embodiment of FIG. 10, the intake orifices 1008 are both 0.25-inch ID holes. Water is withdrawn from the source through the intake orifices 1008 up into the sample tube 1006. The upper end of the sample tube 1006 extending beyond the compression sleeve 960 attaches to a transfer tube (not shown), which is routed to the autosampler 802. The transfer tube has an inner diameter of about 0.375 inches and is made of a material such as polyethylene.

The position of the intake orifices 1008 is controlled by the PLC device 804 as described above. The potentiometer, operating as a positional sensor, may be scaled to meet the parameters for each individual field setting. The full range of the sample arm 928 is about 170 degrees traveling from completely horizontal in the downstream direction to near horizontal in the upstream direction. The exact vertical position of the intake orifices 1008 is determined using a $5^{th}$-order polynomial scaled to represent water depth as a function of voltage, as described above.

Upon initiation of a stormwater-quality sample, the motorized actuator 916 rotates the sample arm 928 from its resting, horizontal position to any vertical depth in the storm sewer 800. The autosampler 802 then operates with normal purge/withdraw cycles to collect a stormwater-quality sample. Once the sample has been acquired, the sample arm 928 fully retracts back to the horizontal position, which removes the sample arm 928 from the flow path. Water discharging past the sample arm 928 as it retracts into the horizontal position clears away any debris that may have accumulated on the sample arm 928 while acquiring the sample.

As discussed above, the inventors have demonstrated that stormwater-quality samples collected from the lower, middle, and upper zones of flow in a storm sewer have sediment concentrations and particle sizes that are vertically stratified, decreasing with increasing distance from the pipe invert. Use of a fixed-point sample intake located near the bottom of a storm sewer can overestimate concentrations of suspended sediment since particles with a high specific density tend to travel along the pipe floor, especially in less turbulent flow, which is a condition commonly found in storm sewers. Limitations associated with fixed-point autosamplers can be overcome by positioning the sample intake orifice such that multiple aliquots are collected throughout the vertical profile of the water column. Integration of these zones into a single composite stormwater-quality sample can produce sediment and sediment-associated constituent concentrations that are more representative of the average condition. Additionally, securing the sample tubing along the pipe wall can create a barrier to flow, causing coarse particles to potentially settle out of suspension, thus causing a zone of sediment enrichment near the sample intake. This impediment is eliminated when using the auxiliary sampling device described herein since it has a small footprint in the flow path while temporarily collecting a sample before fully retracting back to the horizontal position.

From the description above, a number of advantages of the auxiliary sampling device become evident. These advantages include the following:

(a) the auxiliary sampling device allows sample acquisition from one or more points in the water column in a pipe;

(b) the auxiliary sampling device is fully retractable and self-cleaning, which reduces the potential of becoming fouled with debris;

(c) the auxiliary sampling device does not interfere with the natural hydrology of the conveyance because it is fully retractable to a horizontal position;

(d) the auxiliary sampling device is controllable via datalogger or other programming logic control device;

(e) the auxiliary sampling device does not rely on mixing of sediment in flow because samples are taken at multiple depths to provide a composite sample that is more representative of the entire water column; and (f) the auxiliary sampling device is scalable to fit a variety of pipe diameters or site specific conditions.

Accordingly, the auxiliary sampling device described herein provides for the collection of stormwater-quality samples from one or multiple points in the water column. The integration of samples from the entire water column, rather than from a single, fixed point, results in a more accurate representation of stormwater-borne solids.

Thus, it will be appreciated by those skilled in the art that modifications and variations of the present invention are possible without departing from the principles and spirit of the invention, the scope of which is defined in the appended claims and their equivalents.

LIST OF REFERENCE NUMERALS 100 auxiliary sampling device
102 support frame of a first embodiment
104 motorized piston
106 potentiometer
108 sample arm assembly
110 mounting plate of support frame of first embodiment
112 front portion of mounting plate of first embodiment
114 back portion of mounting plate of first embodiment
116 second leg of support frame of first embodiment
118 mounting brackets
120 piston
122 stabilizing channel
124 housing
126 shaft
127 stabilizing channel side plates
128 upper member of stabilizing channel
130 upper end of upper member of stabilizing channel
132 flange extending from upper member of stabilizing channel
134 terminus of piston
136 set screws
138 end cap
140 intake orifices
142 sample tube
146 rear mounting hole
200 side plate of support frame of first embodiment
202 first leg of support frame of first embodiment
204 piston mount
206 potentiometer axle
208 concrete anchors
400 motorized piston mount
500 support frame of a second embodiment
502 mounting plate of support frame of second embodiment
504 front portion of support frame of second embodiment
506 back portion of support frame of second embodiment
508 front legs of support frame of second embodiment
510 back legs of support frame of second embodiment
512 mounting bolt securing motorized piston mount to support frame of second embodiment
514 mounting eyelet of motorized piston
516 center-line anchor slots on support frame of second embodiment
518 holes for lateral-stabilizer bolts on support frame of second embodiment
800 storm sewer
802 autosampler
804 programmable logic control (PLC) device
806 relay
808 acoustic velocity sensor
900 auxiliary sampling device of a third embodiment
902 front end of third embodiment
904 rear end of third embodiment
906 primary support frame of third embodiment
908 center-line anchor slots on primary support frame of third embodiment
910 holes for lateral-stabilizer bolts on primary support frame of third embodiment
912 secondary support frame of third embodiment
914 holes for bolts to attach secondary support frame to primary support frame
916 motorized actuator
918 piston of motorized actuator
920 clevis mounting bracket
922 mounting bolt or pin of clevis mounting bracket
924 fitted sleeve
928 sample arm of third embodiment
930 tensioner
932 tensioner
934 cable
936 cable
938 small pulley
940 small pulley
942 large pulley 946 large pulley
948 pin to connect tensioners to piston
949 mounting bracket
950 pin for mounting bracket
951 mounting bracket
952 mounting bracket
954 pin for mounting bracket
956 pin for mounting bracket
958 pin for mounting bracket
960 compression sleeve
962 L-shaped member of compression sleeve
964 locking plate of compression sleeve
966 screw
968 set screws of compression sleeve
1002 shaft of sample arm
1004 end cap of sample arm
1006 sample tube of sample arm
1008 intake orifices of end cap

GENERAL BIBLIOGRAPHY ON THE SUBJECT

The following bibliography provides citations to the references cited in the above text. The references are provided merely to clarify the description of the present invention and citation of a reference either in the bibliography below or in the specification above is not an admission that any such reference is "prior art" to the invention described herein.
1. Clark, S. E., Siu, C. Y. S., Pitt, R., Roenning, C. D., and Treese, D. P., 2008, Peristaltic pump autosamplers for solids measurement in stormwater runoff, Water Environment Research, v. 80, 9 p.
2. Fowler, G. D., Roseen, R. M., Ballestero, T. P., Guo, Q., and Houle, J., 2009, Sediment monitoring by autosampler in comparison with whole volume sampling for parking lot runoff, ASCE Conf. Proc. 342, 150 (2009).
3. Horowitz, A. J., 1995, The use of suspended sediment and associated trace elements in water quality studies, International Association of Hydrological Sciences Special Publication No 4, 58 p.
4. Selbig, W. R. and Bannerman, R. T., 2007, Evaluation of street sweeping as a stormwater-quality management tool in three residential basins in Madison, Wis., U.S. Geological Survey Scientific Investigations Report 2007-5156, 120 p.
5. Smith, K. P., 2002, Effectiveness of three best management practices for highway-runoff quality along the southeast expressway, Boston, Mass., U.S. Geological Survey Water-Resources Investigations Report 02-4059, 62 p.
6. Teledyne ISCO, 2008, 3700R/3740 refrigerated sampler instruction manual, accessed Dec. 16, 2009, at URL http://www.isco.com/pcfiles/PartPDF3/UP000XKF.pdf.

What is claimed is:

1. A fluid sampling device, comprising:
a support frame;
a motorized actuator, with a piston, attached to an end of the support frame;
a sample arm having an upper end disposed at an end of the support frame opposite the motorized actuator and a lower end with an inlet to receive a fluid sample from a fluid source;
a cable and pulley mechanism connecting the sample arm to the piston; and
a fluid conduit within the sample arm having a fluid intake end connected to the inlet and a fluid discharge end connected to an autosampler,
wherein the cable and pulley mechanism vertically pivots the sample arm when the motorized actuator pushes or retracts the piston to position the inlet at desired positions within the fluid source so that the autosampler collects multiple samples at various depths.

2. The fluid sampling device of claim 1, further comprising a rotation sensor within the motorized actuator to measure the rotational position of the sample arm as the piston extends or retracts.

3. The fluid sampling device of claim 1, wherein the sample arm has a rotation range of about 0 from a horizontal position to about 170 degrees to position the inlet at various depths within the fluid source.

4. The fluid sampling device of claim 3, wherein the sample arm retracts to the horizontal position after sampling is completed to move the sample arm from a flow path of the fluid source.

5. The fluid sampling device of claim 4, wherein the sample arm self-cleans as it retracts to the horizontal position by fluid discharging past the sample arm assembly.

6. The fluid sampling device of claim 1, wherein the sample arm further comprises:
an elongated tube having an upper end and a lower end; and
an end cap attached to the lower end of the elongated tube and having intake orifices that define the inlet; and
a compression sleeve receiving the upper end of the elongated tube, the length of the elongated tube extending from the compression sleeve being adjustable by varying the distance the upper end of the elongated tube is inserted into the compression sleeve.

7. The fluid sampling device of claim 6, wherein the compression sleeve comprises an L-shaped member and an accompanying locking plate, the L-shaped member and the locking plate containing recesses to fit around the upper end of the elongated tube.

8. The fluid sampling device of claim 6, wherein the elongated tube is a streamline tube having a major axis of about 1.18 inches, a minor axis of about 0.5 inches, and a wall thickness of about 0.035 inches.

9. The fluid sampling device of claim 6, wherein the intake orifices are formed on opposing sides of the end cap and are positioned so that the fluid from the fluid source moves parallel to each intake orifice, and a bottom end of the fluid conduit is connected to the endcap and receives the sample fluid through the intake orifices.

10. The fluid sampling device of claim 6, wherein the fluid intake end of the fluid conduit is connected to the end cap and receives the sample fluid through the intake orifices, and the fluid conduit extends from the end cap, through the elongated tube, to the autosampler.

11. The fluid sampling device of claim 6, wherein the cable and pulley mechanism comprises:
a first tensioner and a second tensioner connected respectively to opposite sides of a terminus of the piston;
a first pulley mounted on the support frame in a path from the first tensioner to the sample arm;
a series of pulleys mounted on the support frame in a path from the second tensioner to the sample arm;
a first cable extending from the first tensioner around the first pulley; and
a second cable extending from the second tensioner around the series of pulleys,
wherein movement of the piston is translated into pivotal movement of the sample arm.

12. The fluid sampling device of claim 11, wherein the series of pulleys mounted on the support frame in a path from the second tensioner to the sample arm comprises:
a second pulley, the first pulley and the second pulley being mounted on the support frame at the end of the support frame adjacent to the sample arm and being connected to each side of the compression sleeve of the sample arm;

a third pulley mounted on the support frame near the second tensioner; and a fourth pulley mounted on the support frame near the second pulley.

13. A method of collecting samples from a fluid source using an autosampler, comprising:

assembling an auxiliary sampling device, comprising, providing a support frame having a front end and a rear end, attaching a motorized actuator with a piston to the rear end of the support frame, providing a rotatable sample arm having an upper end disposed at the front end of the support frame and a lower end with an inlet to receive a fluid sample from a fluid source, connecting a cable and pulley mechanism between the sample arm and the piston, and placing a fluid conduit, having a fluid intake end and a fluid discharge end, within the sample arm, and connecting the fluid intake end to the inlet to receive the fluid sample and connecting the fluid discharge end to an autosampler;

controlling the motorized actuator to push or retract the piston, the movement of the piston being translated into pivotal movement of the sample arm to position the inlet at a desired level within the fluid source;

drawing fluid up the fluid conduit to the autosampler; and repeatedly controlling the motorized actuator to position the inlet of the sample arm at various levels within the fluid source to collect multiple samples.

14. The method of claim 13, further comprising mounting the support frame of the fluid sampling device to a ceiling of a storm sewer and rotating the sample arm downward from a horizontal position into the fluid source within the storm sewer to collect the samples.

15. The method of claim 14, further comprising controlling the motorized actuator to retract the sample arm to a horizontal position after sampling is completed to move the sample arm from a flow path of the fluid source.

16. A fluid collection system, comprising:

an autosampler; and an auxiliary sampling device, comprising, a support frame, a motorized actuator, with a piston, attached to an end of the support frame, a sample arm having an upper end disposed at an end of the support frame opposite the motorized actuator and a lower end with an inlet to receive a fluid sample from a fluid source, a cable and pulley mechanism connecting the sample arm to the piston, and a fluid conduit within the sample arm having a fluid intake end connected to the inlet and a fluid discharge end connected to an autosampler, wherein the cable and pulley mechanism vertically pivots the sample arm when the motorized actuator pushes or retracts the piston to position the inlet at desired positions within the fluid source so that the autosampler collects multiple samples at various depths.

17. The fluid collection system of claim 16, further comprising:

a controller to control the motorized actuator to rotate the sample arm through the cable and pulley mechanism to position the inlet within the fluid source, and to control operation of the autosampler to draw the fluid through the fluid conduit and into a storage container; and a rotation sensor to measure the rotational position of the sample arm.

18. The fluid collection system of claim 17, wherein the controller controls the motorized actuator to rotate the sample arm assembly through the cable and pulley mechanism until the inlet is positioned at a predetermined percentage of the depth of the fluid source.

19. The fluid collection system of claim 17, further comprising a fluid level sensor to measure a depth of the fluid source and communicate same to the controller.

20. The fluid collection system of claim 19, wherein the controller receives the fluid depth measurement from the fluid level sensor, determines a voltage representing the fluid depth and a target voltage representing a target depth, and activates the motorized actuator to extend or retract the piston, the movement of the piston translating into rotation of the sample arm through the cable and pulley mechanism until the rotation sensor reaches the target voltage.

* * * * *